(12) United States Patent
Wrobel et al.

(10) Patent No.: US 10,449,064 B2
(45) Date of Patent: Oct. 22, 2019

(54) STENT WITH ANTI-MIGRATION FEATURE

(71) Applicant: BOSTON SCIENTIFIC SCIMED, INC., Maple Grove, MN (US)

(72) Inventors: Thomas A. Wrobel, Long Lake, MN (US); Ravi Ramrakhyani, Boston, MA (US); Jason Weiner, Grafton, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 150 days.

(21) Appl. No.: 15/041,765

(22) Filed: Feb. 11, 2016

(65) Prior Publication Data

US 2016/0235561 A1 Aug. 18, 2016

Related U.S. Application Data

(60) Provisional application No. 62/115,284, filed on Feb. 12, 2015.

(51) Int. Cl.
| | |
|---|---|
| *A61F 2/848* | (2013.01) |
| *A61F 2/24* | (2006.01) |
| *A61F 2/90* | (2013.01) |
| *A61F 2/07* | (2013.01) |
| *A61F 2/958* | (2013.01) |

(52) U.S. Cl.
CPC .......... *A61F 2/848* (2013.01); *A61F 2/2418* (2013.01); *A61F 2/90* (2013.01); *A61F 2/07* (2013.01); *A61F 2/958* (2013.01); *A61F 2210/0076* (2013.01); *A61F 2250/001* (2013.01)

(58) Field of Classification Search
CPC .... A61F 2/07; A61F 2/90; A61F 2/958; A61F 2250/001; A61F 2/95; A61F 2/848; A61F 2250/0004; A61F 2/962; A61F 2/966
See application file for complete search history.

(56) References Cited

U.S. PATENT DOCUMENTS

| | | |
|---|---|---|
| 4,141,364 A | 2/1979 | Schultze |
| 4,728,328 A | 3/1988 | Hughes et al. |
| 5,522,881 A | 6/1996 | Lentz |
| 5,575,818 A | 11/1996 | Pinchuk |
| 5,667,523 A | 9/1997 | Bynon et al. |
| 5,723,003 A | 3/1998 | Winston et al. |
| 5,725,547 A | 3/1998 | Chuter |
| 5,725,549 A | 3/1998 | Lam |
| 5,735,872 A * | 4/1998 | Carpenter ............... A61F 2/93 606/198 |
| 5,824,046 A | 10/1998 | Smith et al. |
| 6,010,530 A * | 1/2000 | Goicoechea ............ A61F 2/07 623/1.13 |
| 6,027,525 A | 2/2000 | Suh et al. |
| 6,036,725 A | 3/2000 | Avellanet |
| 6,048,360 A | 4/2000 | Khosravi et al. |
| 6,143,022 A | 11/2000 | Shull et al. |

(Continued)

*Primary Examiner* — Ryan J. Severson
*Assistant Examiner* — Christian D Knauss
(74) *Attorney, Agent, or Firm* — Seager, Tufte & Wickhem, LLP

(57) ABSTRACT

A tubular stent includes a stent body having a distal end and a proximal end, a covering surrounding at least a portion of the stent body and an adjustable annular ring secured to the stent body. The adjustable annular ring is configured to permit radial expansion of the adjustable annular ring while resisting radial compression of the adjustable annular ring.

18 Claims, 13 Drawing Sheets

(56) References Cited

U.S. PATENT DOCUMENTS

| | | | |
|---|---|---|---|
| 6,436,132 B1* | 8/2002 | Patel | A61F 2/07 623/1.13 |
| 7,083,640 B2 | 8/2006 | Lombardi et al. | |
| 7,223,284 B2 | 5/2007 | Khosravi et al. | |
| 7,641,683 B2 | 1/2010 | Khosravi et al. | |
| 7,655,034 B2 | 2/2010 | Mitchell et al. | |
| 8,128,677 B2 | 3/2012 | Schneider et al. | |
| 9,060,890 B2 | 6/2015 | Bingener-Casey et al. | |
| 2003/0009211 A1 | 1/2003 | DiCarlo | |
| 2003/0158595 A1 | 8/2003 | Randall et al. | |
| 2004/0030381 A1* | 2/2004 | Shu | A61F 2/2409 623/2.11 |
| 2006/0212113 A1* | 9/2006 | Shaolian | A61F 2/07 623/1.35 |
| 2006/0229714 A1 | 10/2006 | Lombardi et al. | |
| 2007/0135904 A1* | 6/2007 | Eidenschink | A61F 2/82 623/1.35 |
| 2007/0142907 A1* | 6/2007 | Moaddeb | A61F 2/2418 623/2.11 |
| 2009/0030501 A1* | 1/2009 | Morris | A61F 2/915 623/1.15 |
| 2010/0076548 A1* | 3/2010 | Konno | A61F 2/2412 623/2.1 |
| 2011/0004237 A1 | 1/2011 | Schneider et al. | |
| 2014/0249623 A1 | 9/2014 | Matheny | |
| 2016/0038318 A1 | 2/2016 | Weier et al. | |

* cited by examiner

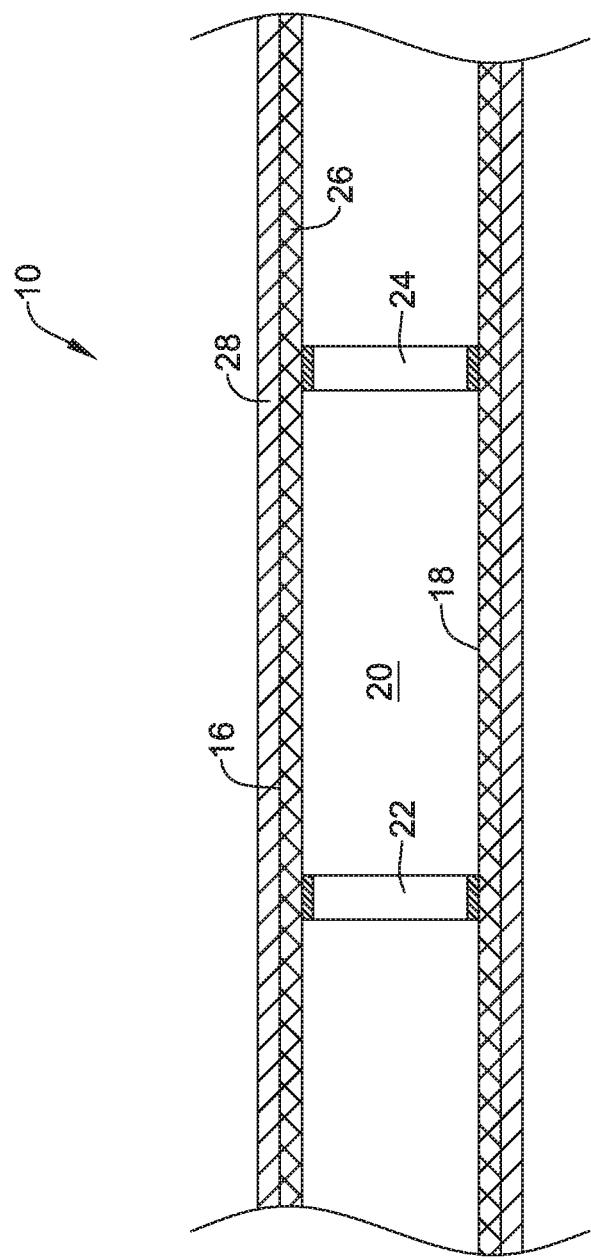

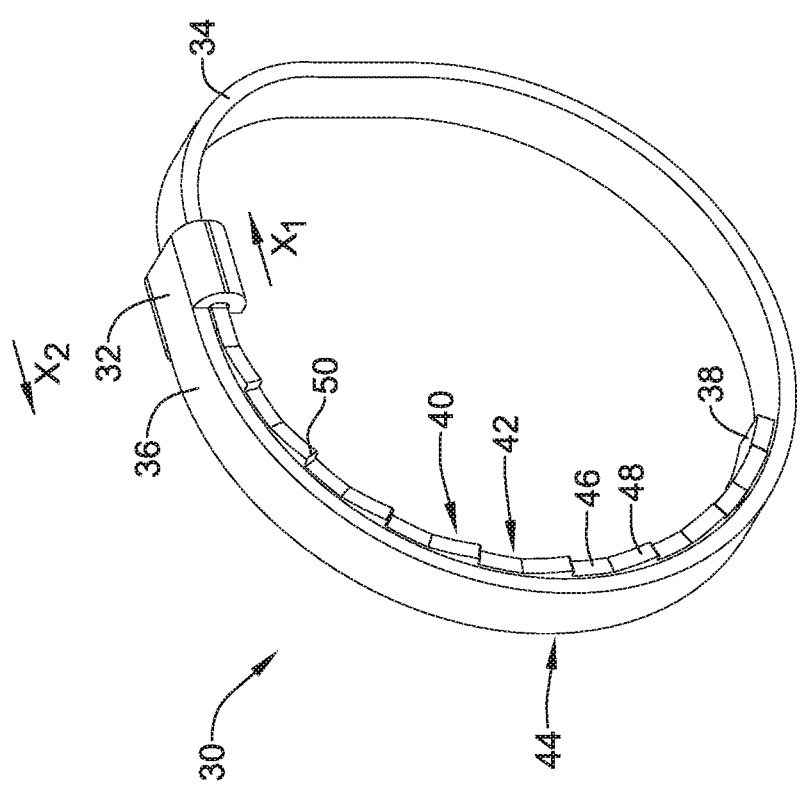

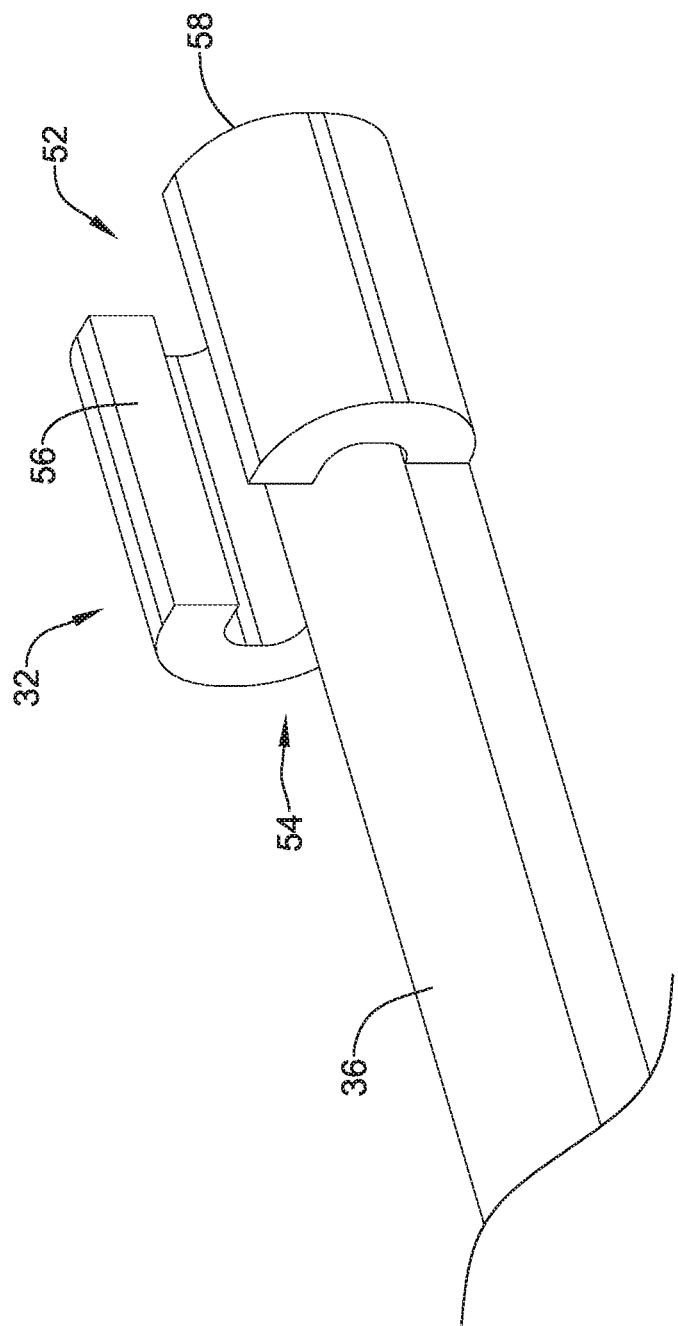

STENT WITH ANTI-MIGRATION FEATURE

CROSS-REFERENCE TO RELATED APPLICATIONS

This application claims priority under 35 U.S.C. § 119(e) to U.S. Provisional Application No. 62/115,284, filed Feb. 12, 2015, the entire disclosure of which is herein incorporated by reference.

TECHNICAL FIELD

The disclosure is directed to an endoprosthesis, such as a stent. More particularly, the disclosure is directed to a stent including one or more anti-migration features.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. A variety of different stents have been developed, and may be manufactured by any one of a variety of different manufacturing methods and may be used according to any one of a variety of methods. Of the known medical devices and methods, each has certain advantages and disadvantages.

SUMMARY

The disclosure is directed to several alternative designs, materials and methods of manufacturing medical device structures and assemblies, and uses thereof.

In one example, a tubular stent includes a stent body having a distal end and a proximal end, a covering surrounding at least a portion of the stent body and an adjustable annular ring secured to the stent body. The adjustable annular ring is configured to permit radial expansion of the adjustable annular ring while resisting radial compression of the adjustable annular ring.

Alternatively or additionally to any of the embodiments above, the stent body is expandable, and the adjustable annular ring is configured to expand in response to an expansive force applied to the stent body.

Alternatively or additionally to any of the embodiments above, the stent body is expandable from a compressed configuration having a first diameter to an expanded configuration having a second diameter, and the adjustable annular ring is configured to expand to a diameter greater than the second diameter.

Alternatively or additionally to any of the embodiments above, the stent body includes a braided structure including a plurality of wires braided together, and the adjustable annular ring is mechanically secured relative to the braided structure.

Alternatively or additionally to any of the embodiments above, the adjustable annular ring is adhesively secured to the stent body.

Alternatively or additionally to any of the embodiments above, the adjustable annular ring includes a head and an elongate portion having a first end secured to the head and a second end that is passable through the head.

Alternatively or additionally to any of the embodiments above, the elongate portion interacts with the head such that the elongate portion is permitted to move in a first direction through the head but is prevented from moving in a second, opposite, direction through the head.

Alternatively or additionally to any of the embodiments above, the elongate portion has a rectilinear cross-sectional profile extending circumferentially around the stent body.

Alternatively or additionally to any of the embodiments above, the elongate portion includes a plurality of angled teeth formed in at least one side of the elongate portion.

In another example, a stent that is configured to resist migration once implanted includes a support structure extending from a distal end to a proximal end, the support structure defining an inner surface. A first adjustable anti-migration ring is secured relative to the inner surface of the support structure and a second adjustable anti-migration ring that is spaced apart from the first anti-migration ring is secured relative to the inner surface of the support structure. The first and second adjustable anti-migration rings are configured to permit radial expansion thereof while resisting radial compression thereof.

Alternatively or additionally to any of the embodiments above, the support structure includes a braided metal structure or a laser cut tubular support structure.

Alternatively or additionally to any of the embodiments above, the stent further includes a covering surrounding at least a portion of the support structure.

Alternatively or additionally to any of the embodiments above, the support structure is expandable from a compressed configuration having a first diameter to an expanded configuration having a second diameter, and the first and second anti migration rings are configured to radially expand beyond the second diameter of the support structure.

Alternatively or additionally to any of the embodiments above, each of the first anti-migration ring and the second anti-migration ring include a head including a ratchet mechanism and an elongate portion having a first end secured to the head and a second end that is passable through the head, the elongate portion including an integrated gear rack that is configured to interact with the ratchet mechanism such that the elongate portion is permitted to move in a first direction through the head but is prevented from moving in a second, opposite, direction through the head.

Alternatively or additionally to any of the embodiments above, the elongate portion has a rectilinear cross-sectional profile extending circumferentially around the support structure and the integrated gear rack comprises a plurality of angled teeth formed in at least one side of the elongate portion.

In another example, a tubular stent includes a stent body having a distal end and a proximal end, a covering surrounding at least a portion of the stent body and an adjustable annular ring secured to the stent body. The adjustable annular ring is configured to permit radial expansion of the adjustable annular ring while resisting radial compression of the adjustable annular ring.

Alternatively or additionally to any of the embodiments above, the stent body is expandable, and the adjustable annular ring is configured to expand in response to an expansive force applied to the stent body.

Alternatively or additionally to any of the embodiments above, the stent body is expandable from a compressed configuration having a first diameter to an expanded configuration having a second diameter, and the adjustable annular ring is configured to expand to a diameter greater than the second diameter.

Alternatively or additionally to any of the embodiments above, the stent body includes a braided structure including a plurality of wires braided together, and the adjustable annular ring is secured relative to the stent body via at least one of the plurality of wires passing through the adjustable annular ring.

Alternatively or additionally to any of the embodiments above, the adjustable annular ring is adhesively secured to the stent body.

Alternatively or additionally to any of the embodiments above, the adjustable annular ring includes a head and an elongate portion having a first end secured to the head and a second end that is passable through the head.

Alternatively or additionally to any of the embodiments above, the elongate portion interacts with the head such that the elongate portion is permitted to move in a first direction through the head but is prevented from moving in a second, opposite, direction through the head.

Alternatively or additionally to any of the embodiments above, the elongate portion has a rectilinear cross-sectional profile extending circumferentially around the stent body.

Alternatively or additionally to any of the embodiments above, the integrated gear rack includes a plurality of angled teeth formed in at least one side of the elongate portion.

In another example, a stent that is configured to resist migration once implanted includes a support structure extending from a distal end to a proximal end, the support structure defining an inner surface. A first adjustable anti-migration ring is secured relative to the inner surface of the support structure and a second adjustable anti-migration ring that is spaced apart from the first anti-migration ring is secured relative to the inner surface of the support structure. The first and second adjustable anti-migration rings are configured to permit radial expansion thereof while resisting radial compression thereof.

Alternatively or additionally to any of the embodiments above, the support structure includes a braided metal structure.

Alternatively or additionally to any of the embodiments above, the support structure includes a laser cut tubular support structure.

Alternatively or additionally to any of the embodiments above, the stent further includes a covering surrounding at least a portion of the support structure.

Alternatively or additionally to any of the embodiments above, the support structure is expandable from a compressed configuration having a first diameter to an expanded configuration having a second diameter, and the first and second anti migration rings are configured to radially expand beyond the second diameter of the support structure.

Alternatively or additionally to any of the embodiments above, each of the first anti-migration ring and the second anti-migration ring include a head including a ratchet mechanism and an elongate portion having a first end secured to the head and a second end that is passable through the head, the elongate portion including an integrated gear rack that is configured to interact with the ratchet mechanism such that the elongate portion is permitted to move in a first direction through the head but is prevented from moving in a second, opposite, direction through the head.

Alternatively or additionally to any of the embodiments above, the elongate portion has a rectilinear cross-sectional profile extending circumferentially around the support structure.

Alternatively or additionally to any of the embodiments above, the integrated gear rack includes a plurality of angled teeth formed in at least one side of the elongate portion.

In another example, a stent including a support structure and an anti-migration ring secured relative to the support structure is deployed within a body lumen of a patient, such as the patient's esophagus. The stent is advanced to a desired position within the body lumen (e.g., esophagus) while the stent is in a radially compressed configuration. The stent is expanded from the radially compressed configuration to a radially expanded configuration in the body lumen and is secured in place in the body lumen by further radially expanding the anti-migration ring.

Alternatively or additionally to any of the embodiments above, expanding the stent from the compressed configuration to the radially expanded configuration includes expanding the stent using an inflatable balloon.

Alternatively or additionally to any of the embodiments above, securing the stent in place by further radially expanding the anti-migration ring includes expanding the anti-migration ring using the inflatable balloon.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The aspects of the disclosure may be further understood in consideration of the following detailed description of various embodiments in connection with the accompanying drawings, in which:

FIG. 2A is a longitudinal cross-sectional view of the stent of FIG. 1;

FIG. 3 is a perspective of an anti-migration ring forming part of the stent of FIG. 1;

FIG. 4 is a perspective view of a portion of the anti-migration ring of FIG. 3;

Figure 1:
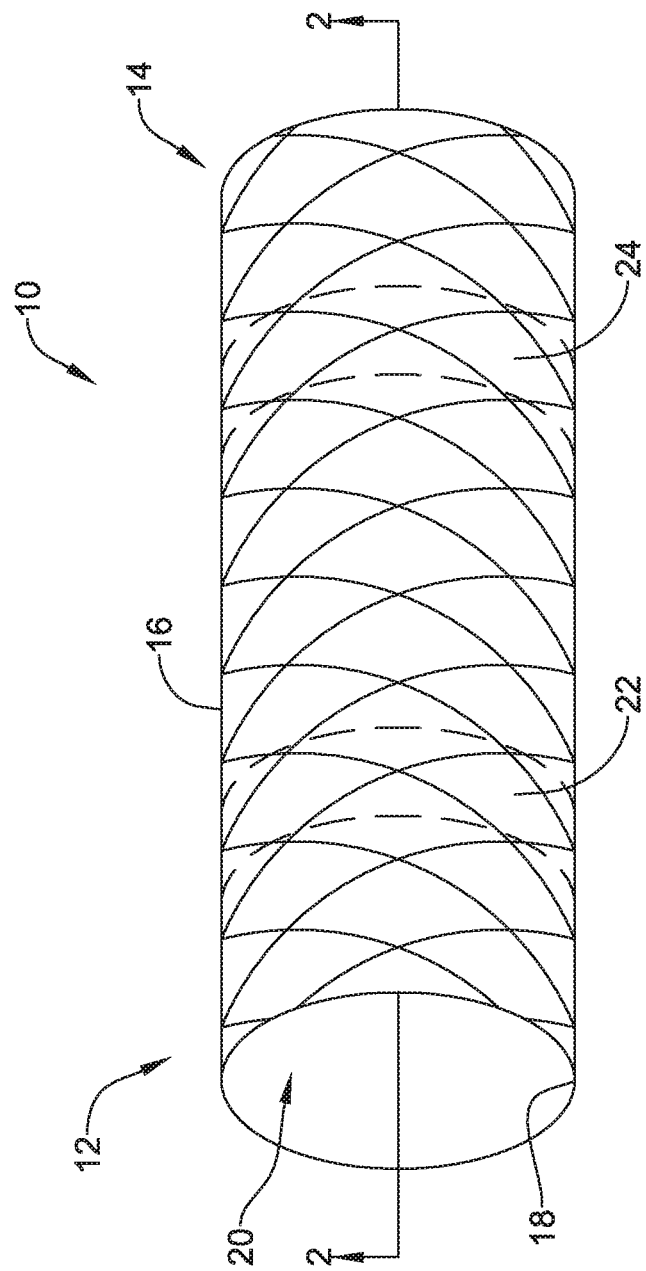
FIG. 1 is a perspective view of an illustrative stent in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a perspective view of an illustrative endoprosthesis 10. While the endoprosthesis 10 is described herein as being a stent 10 useful as an esophageal stent, it will be appreciated that various features of the stent 10, including its anti-migration features to be described herein, are applicable to any variety of different stents intended for deployment in a variety of different body systems and locations. The stent 10 extends from a first, proximal end 12 to a second, distal end 14 and includes an outer surface 16 and an inner surface 18 defining a lumen 20 extending through the stent 10. It will be appreciated that the terms distal and proximal are generally defined in terms of relative position within the body. Accordingly, it should be understood that references to distal and proximal in describing the stent 10 when not deployed are merely arbitrary, as the stent 10 could be used in any orientation. In some embodiments, the stent 10 may have a single layer construction or a multi-layer construction. In some cases, the construction details of the stent 10 may vary, depending on the intended use of the stent 10.

In some embodiments, the stent 10 may be configured to help resist migration once implanted. As shown in FIG. 1, the stent 10 includes a first anti-migration feature 22 and a second anti-migration feature 24, shown in phantom as the anti-migration features 22, 24 are, in this embodiment, internal to the stent 10 and thus not expressly visible in this illustration. While a pair of anti-migration features 22, 24 are illustrated, it will be appreciated that in some cases, the stent 10 may include only a single anti-migration feature, or perhaps may include three or more anti-migration features. In some instances, the relative number of anti-migration features included in the stent 10 may depend in part upon the intended use of the stent 10, as well as its size. For example, a smaller stent, or a stent intended for deployment in a relatively calm body environment, may only have a single anti-migration feature. A larger stent, or a stent intended for deployment in a less calm body environment, may include two, three or more anti-migration features.

FIG. 2A is a longitudinal cross-sectional view of the stent 10, taken along the line 2-2 in FIG. 1. As illustrated, the stent 10 includes a support structure 26 and a covering 28 that extends over at least a portion of the support structure 26. While generically illustrated, the support structure 26 may be a woven support structure such as a metal braid or a laser cut tubular support structure, for example. In some embodiments, the covering 28 may be a polymeric covering and, as illustrated, be a single polymeric layer. In some cases, the covering 28 may include two or more distinct polymeric layers. In some embodiments, the covering 28 may include or otherwise be a non-polymeric covering such as a fabric covering or a textile covering. Optionally, the covering 28 may be absent. Although illustrated as surrounding the radially outer surface 16 of the support structure 26, in some instances the covering 28 may surround the radially inner surface 18 of the support structure 26, for example.

In some embodiments, the anti-migration features 22, 24 may be disposed proximate the inner surface 18, the outer surface 16, and/or other region of the stent 10. In some instances, the anti-migration features 22, 24 may be adhesively secured to the support structure 26, such as the inner surface 18, perhaps at a single location on each of the anti-migration features 22, 24 to permit relative movement as the anti-migration features 22, 24 change in diameter. In other words, each of the anti-migration features 22, 24 may be secured to the support structure 26 along less than the entire circumference of the anti-migration features 22, 24, such that the remainder of the circumference of the anti-migration features 22, 24 may move relative to the support structure 26. In some cases, a winding or wire forming part of the support structure 26 may pass through and secure the anti-migration features 22, 24. The anti-migration features 22, 24 may be annular rings that are configured to expand in diameter in response to an applied expansive force but to resist reduction in diameter in response to an applied compressive force.

Figure 2B:
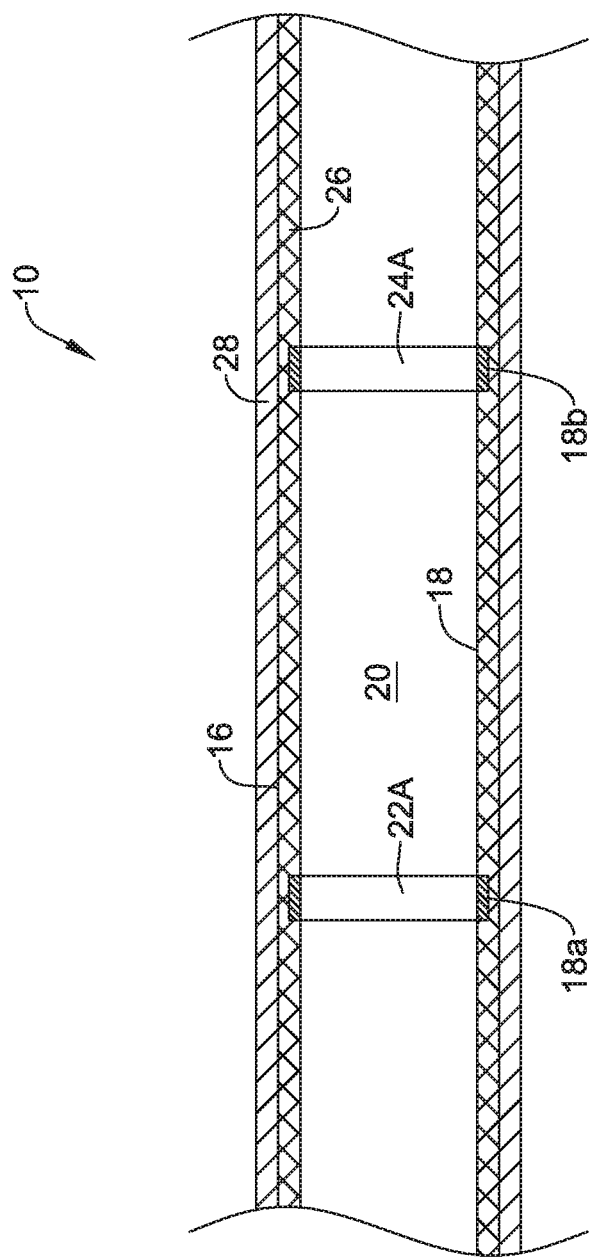
FIG. 2B is an alternate longitudinal cross-sectional view of the stent of FIG. 1.

In some embodiments, as illustrated for example in FIG. 2B, the inner surface 18 may include a first notch or recess 18A and a second notch or recess 18B. In some instances, an anti-migration ring 22A may fit into the first notch or recess 18A while an anti-migration ring 24A may fit into the second notch or recess 18B. As will be appreciated, the first notch or recess 18A and/or the second notch or recess 18B may extend circumferentially about the inner surface 18 and may help to locate and/or secure the anti-migration ring 22A and/or the anti-migration ring 24A in position. In some instances, the first notch or recess 18A and/or the second notch or recess 18B, if present, may allow the anti-migration rings 22A, 24A to not intrude as far into the lumen 20 or not extend into the lumen 20 to obstruct the lumen 20. In some cases, the notches or recesses 18A, 18B may themselves be sufficient to hold the anti-migration rings 22A, 24A in position. In some instances, an additional securement mechanism may be used, such as but not limited to a spot weld or a spot of adhesive on each of the anti-migration rings 22A, 24A at one or more discrete fixation points.

FIG. 3 provides an illustrative but non-limiting example of a suitable anti-migration feature. In FIG. 3, an anti-migration ring 30 is illustrated. The anti-migration ring 30 is largely annular in overall shape, and may be considered as including a head 32 and an elongate portion 34. The elongate portion 34 has a first end 36 that is secured to the head 32 and a second end 38 that is passable through the head 32. In some embodiments, the elongate portion 34 interacts with the head 32 such that the elongate portion 34 is permitted to move in a first direction through the head 32 but is prevented from moving in a second, opposite, direction through the head 32. As illustrated, the elongate portion 34 is able to move in a first direction labeled X1 through the head 32 to enlarge the circumference of the anti-migration ring 30, but is prevented from moving in a second direction labeled X2 through the head 32 to reduce the circumference of the anti-migration ring 30. As a result, the anti-migration ring 30 may be enlarged in diameter but resists reductions in diameter.

In some embodiments, as illustrated, the elongate portion 34 has a rectilinear cross-sectional profile extending circumferentially around the anti-migration ring 30, and thus around the stent 10. At least the end region of the elongate portion 34 proximate the second end 38 of the elongate portion 34 includes an integrated gear rack 40 that interacts with the head 32 to permit one way movement. In some embodiments, the anti-migration ring 30 includes the integrated gear rack 40 on a first side 42 of the elongate portion 34 as well as another integrated gear rack (not visible) on a second side 44 of the elongate portion 34. In some embodiments, as illustrated, the integrated gear rack 40 includes a series of alternating flat spots 46 and angled teeth 48. A lip 50 is formed at one end of each of the angled teeth 48. In looking at the head 32 (see FIG. 4), it can be seen that the head 32 includes a ratchet mechanism 52 that interacts with the integrated gear rack 40.

The head 32 includes a void 54 sized to accommodate the end region proximate the second end 38 of the elongate portion 34. A slot 56, which extends through the head 32 to the void 54, permits the ratchet mechanism 52 to flex somewhat, thereby permitting the elongate portion 34 to pass through the head 32 in the X1 direction. It will be appreciated that the lip 50 will strike a flat face 58 on either side of the void 54, thereby resisting movement in the X2 direction. Accordingly, the anti-migration ring 30 may grow in diameter in response to an applied expansive force but will resist any reduction in diameter in response to an applied compressive force.

It will be appreciated that the stent 10 (FIG. 1) may be considered as having a first diameter when in a compressed configuration for delivery, for example, and a second, larger diameter when in an expanded configuration. The relative differences in first diameter and second diameter may vary, depending on the size of the stent 10 and its intended use and deployment location. In some embodiments, the anti-migration ring 30 is configured such that it can be expanded to a diameter that is greater than the second diameter, i.e., the diameter of the expanded stent 10. As a result, the anti-migration ring 30, or a plurality of anti-migration rings 30, can be expanded to a larger diameter that helps prevent migration of the stent 10.

Figure 10:
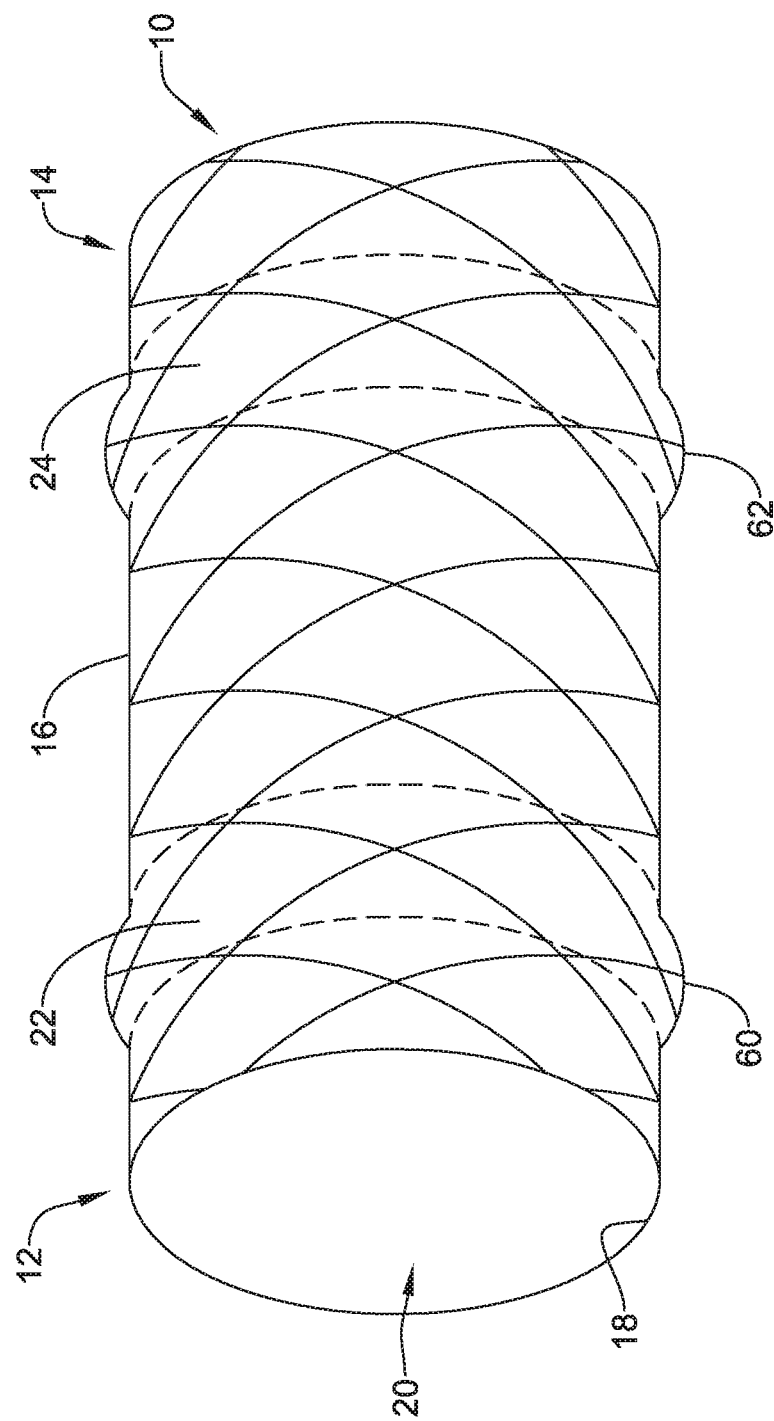
FIG. 10 is a side view of the stent of FIG. 1 after implantation.

This can be seen, for example, in FIG. 10, which illustrates the stent 10 after deployment and expansion of the stent 10 as well as further expansion of the anti-migration rings 22, 24. In FIG. 10, it can be seen that the outer surface 16 of the stent 10 includes an enlarged portion 60 corresponding to the location of the first anti-migration ring 22 and an enlarged portion 62 corresponding to the location of the second anti-migration ring 24.

Figure 5:
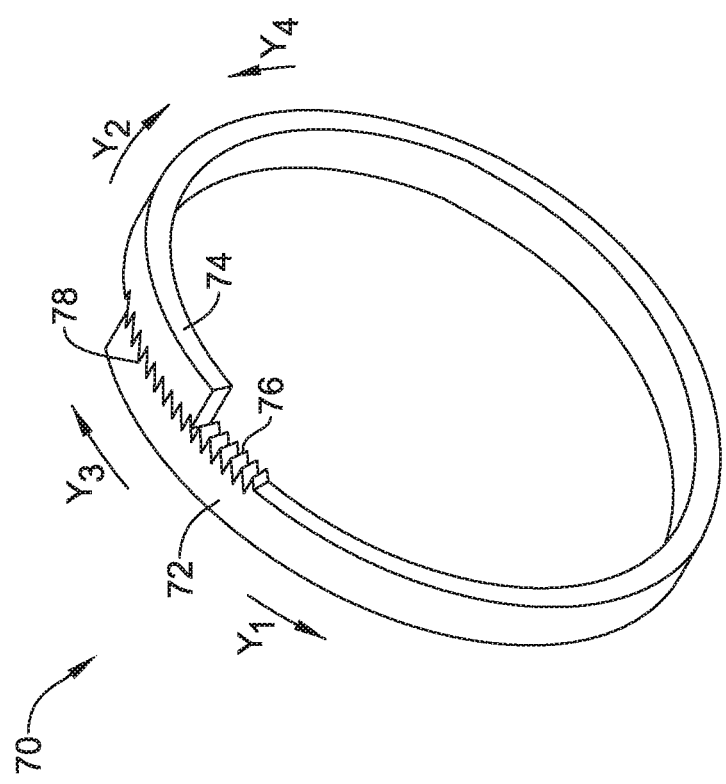
FIG. 5 is a perspective view of an anti-migration ring in accordance with an embodiment of the disclosure.
Figure 6:
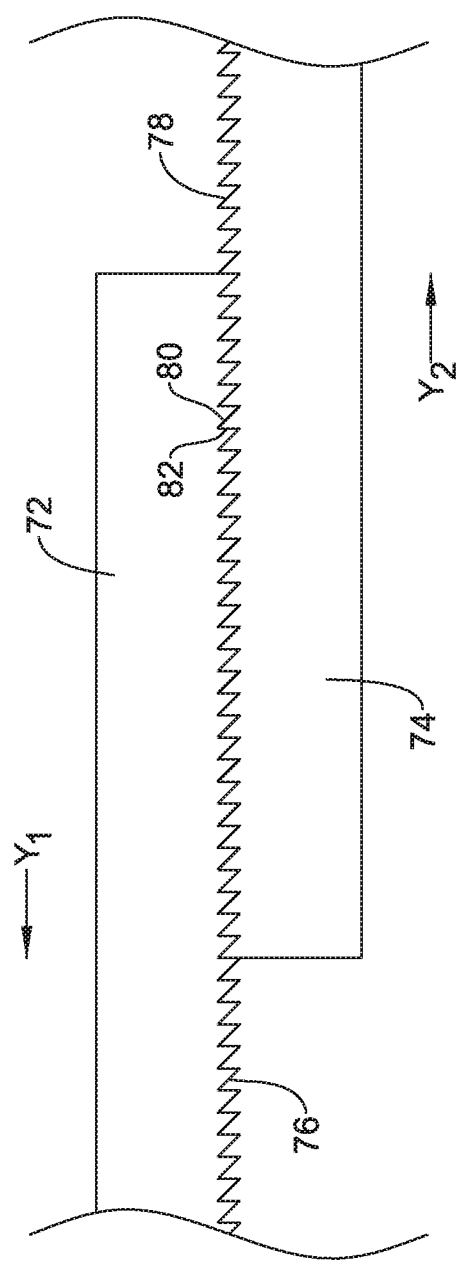
FIG. 6 is an enlarged view of a portion of the anti-migration ring of FIG. 5.

FIG. 5 provides a perspective view of an anti-migration ring 70 and FIG. 6 provides an enlarged view of a portion thereof. Rather than having a head and tail, such as the anti-migration ring 30, the anti-migration ring 70 takes the form of a key ring, having a first end region proximate a first end 72 movable relative to a second end region proximate a second end 74. The first end region may circumferentially overlap with the second end region. The first end region proximate the first end 72 includes a keyed surface 76 and the second end region proximate the second end 74 includes a keyed surface 78. As can be seen in FIG. 6, the individual teeth on the keyed surface 76 and the individual teeth on the keyed surface 78 are angled in such a way as to permit relative movement between the first end region and the second end region in a first direction yet resist relative movement in an opposing second direction. To illustrate, the first end 72 may move in a direction labeled Y1 relative to the second end 74 and the second end 74 may move in a direction labeled Y2 relative to the first end 72 to enlarge the circumference of the anti-migration ring 70, while the first end 72 is prevented from moving in a direction labeled Y3 relative to the second end 74 and the second end 74 is prevented from moving in a direction labeled Y4 relative to the first end 72 to reduce the circumference of the anti-migration ring 70. Each individual tooth has an angled surface 80 and a more steeply angled surface or vertical surface 82. It will be appreciated that in response to an applied expansive force, the angled surfaces 80 of the teeth will permit movement in the Y1 direction. In response to an applied compressive force, the vertical surfaces 82 of each tooth will resist relative movement between the first end 72 and the second end 74 in the Y3 direction and Y4 direction, respectively.

Figure 7:
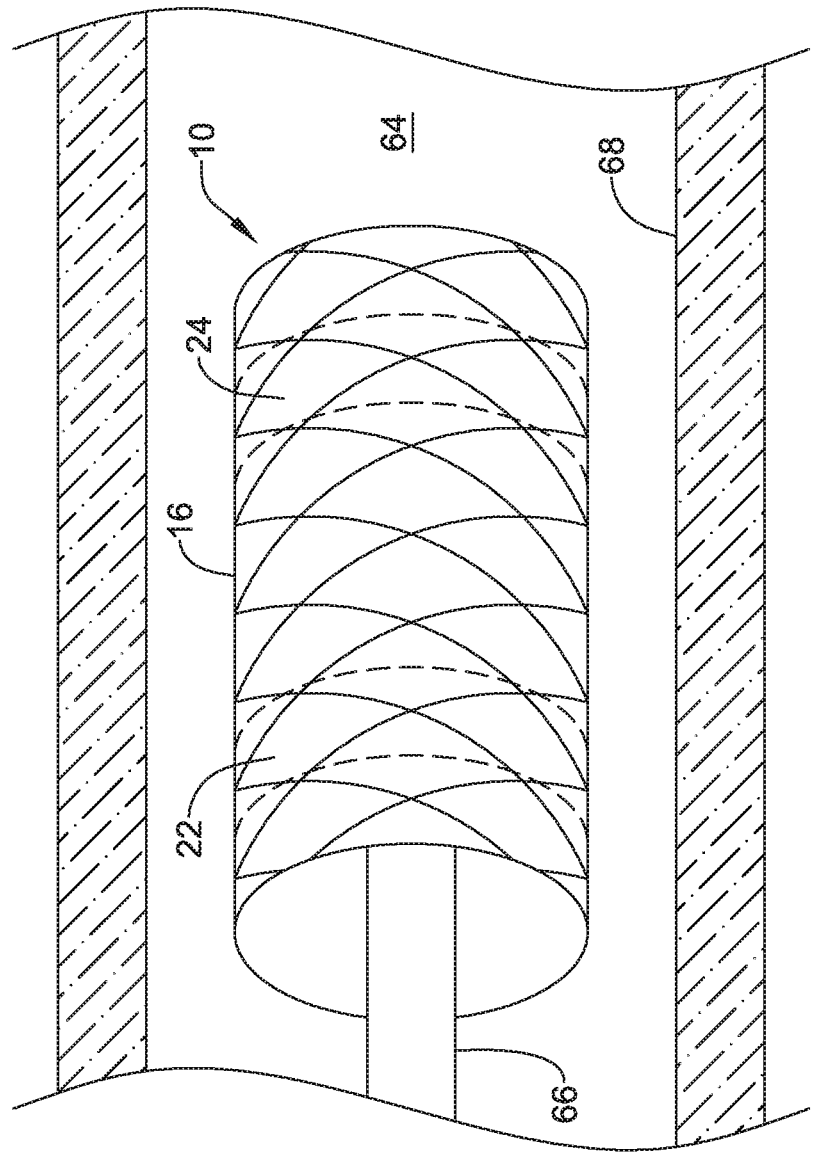
FIGS. 7-9 illustrate an implantation method for implanting the stent of FIG. 1.
Figure 8:
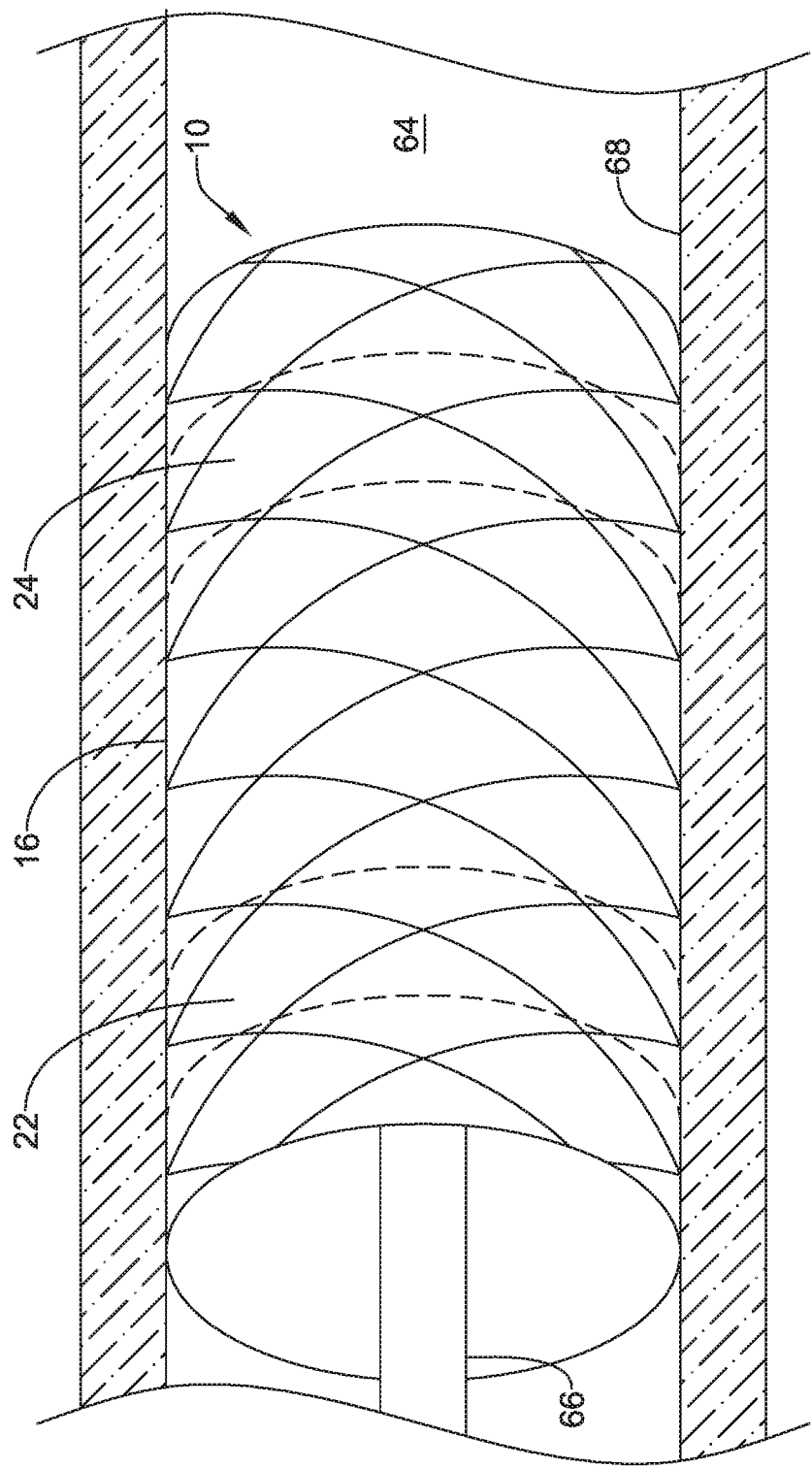
Figure 9:
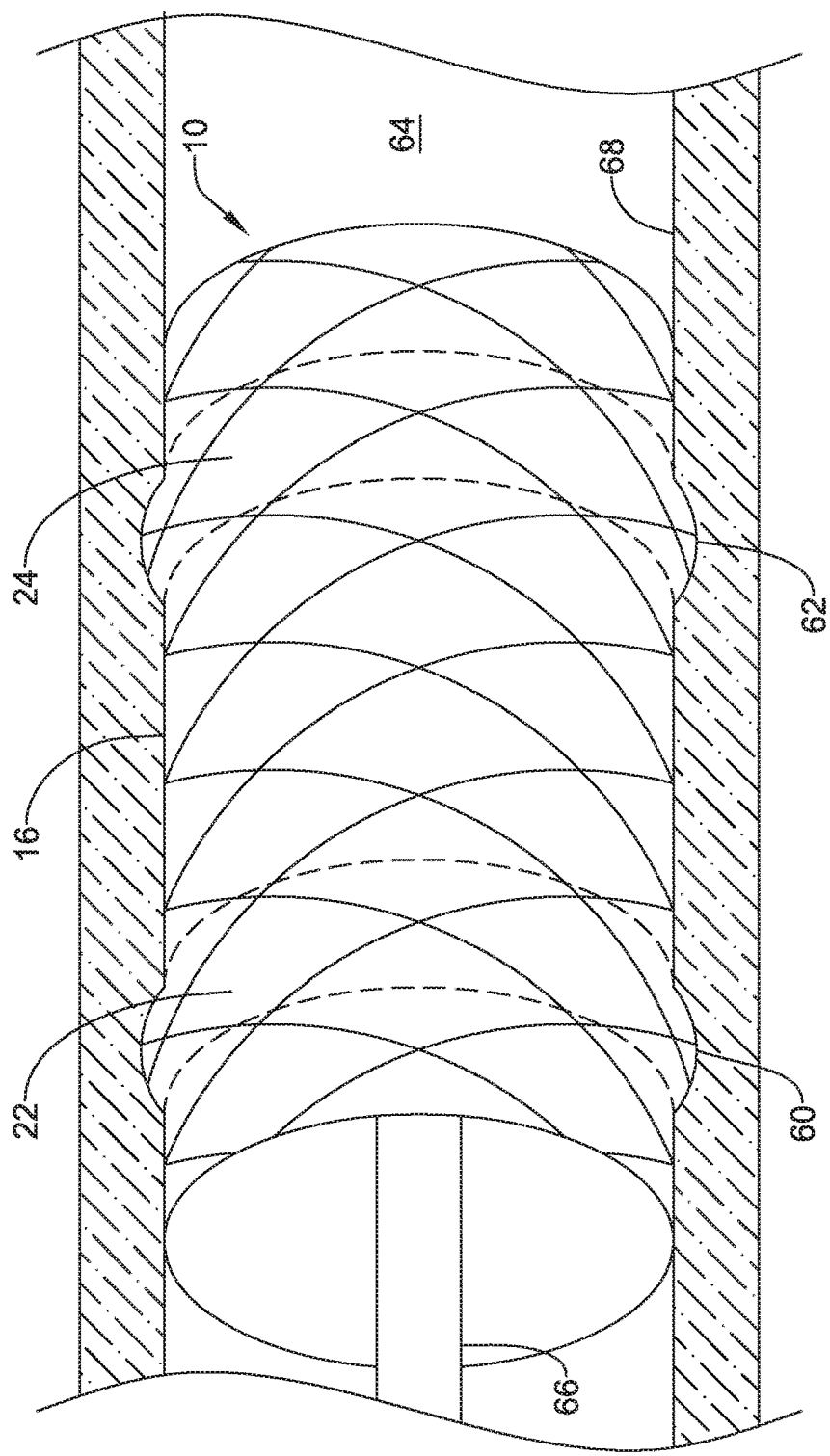

The stent 10 may be deployed in any suitable fashion, depending on its intended use and destination within the body. FIGS. 7-9 generically illustrate deployment of the stent 10 within a body lumen 64. In FIG. 7, the stent 10 is in a compressed configuration for delivery, and is shown deployed on a delivery catheter 66. In some embodiments, the stent 10 may be self-expanding, and thus the delivery catheter 66 would further include an outer sheath holding the stent 10 in its compressed configuration. In some embodiments, the stent 10 is balloon-expandable, and thus the delivery catheter 66 would include an inflatable balloon within the stent 10. In FIG. 8, the stent 10 has been expanded such that the outer surface 16 of the stent 10 is roughly in contact with an inner surface 68 of the body lumen 64. The anti-migration rings 22, 24 may radially expand as the support structure 26 of the stent 10 expands, or subsequently. Finally, in FIG. 9, the anti-migration rings 22, 24 have been further expanded such that the enlarged portions 60 and 62, overlying the anti-migration rings 22, 24, extend radially outward farther than other areas of the stent 10. As a result, the enlarged portions 60 and 62 are able to further engage the inner surface 68 of the body lumen 64 in order to resist migration.

Figure 11B:
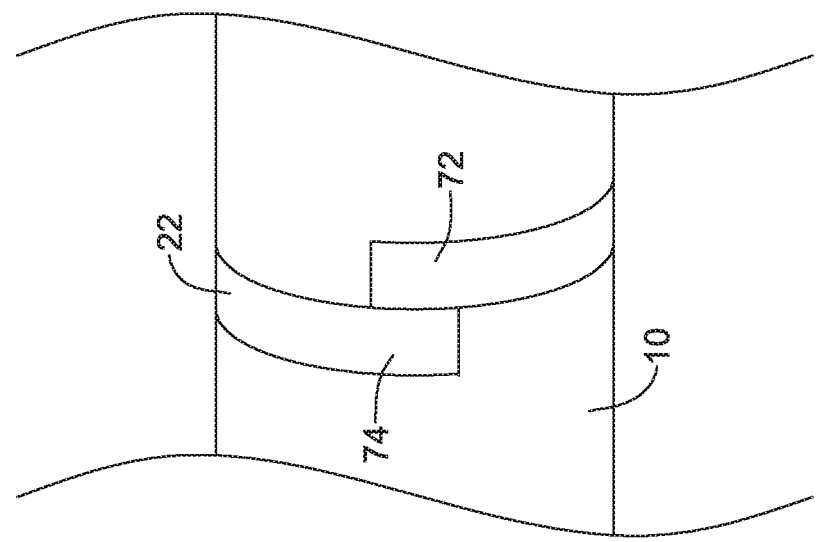
FIGS. 11A-B illustrate a method for subsequently removing the stent of FIG. 1.
Figure 11A:
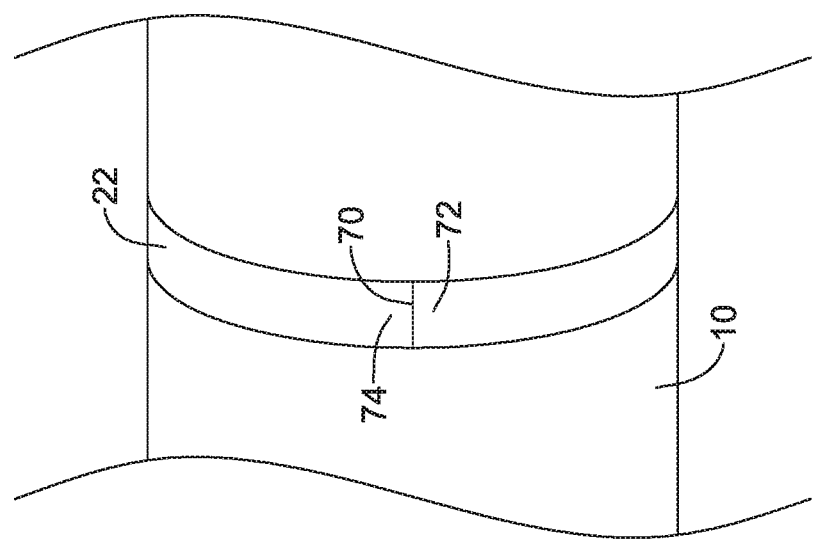

In some embodiments, there may be a desire to remove the stent 10 at some point in the future after initial implantation. In some cases, the stent 10 may be removed by cutting the anti-migration rings 22, 24. FIGS. 11A and 11B illustrate a removal process in which an anti-migration ring has been cut. In FIG. 11A, a cut 70 has been made through the anti-migration ring 22, forming a first cut end 72 and a second cut end 74. It will be appreciated that reference to the anti-migration ring 22 in this Figure is illustrative only, as these removal techniques would be applicable to any and all of the anti-migration rings within the stent 10. As can be seen in FIG. 11B, forming the cut 70 may cause the anti-migration ring 22 to reduce in diameter, as the first cut end 72 has overlapped the second cut end 74. This permits the stent 10 to reduce in diameter for easier removal.

Figure 12A:
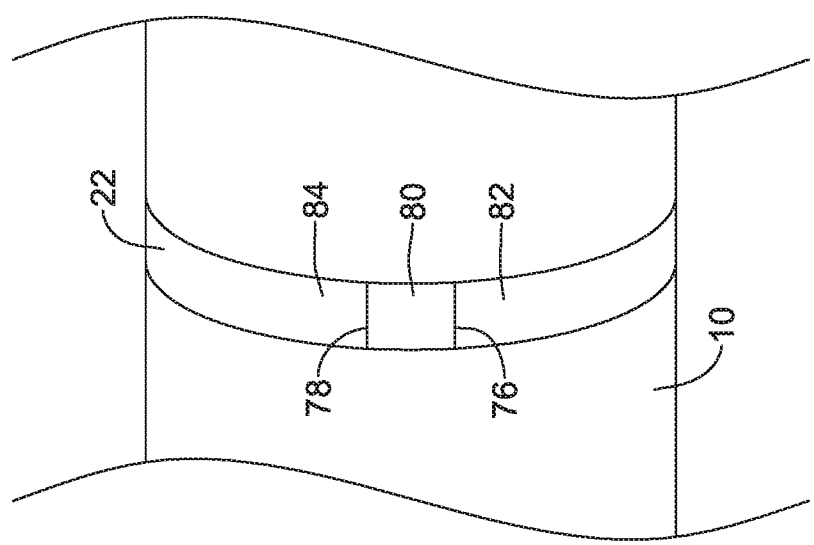
FIGS. 12A-B illustrate a method for subsequently removing the stent of FIG. 1.
Figure 12B:
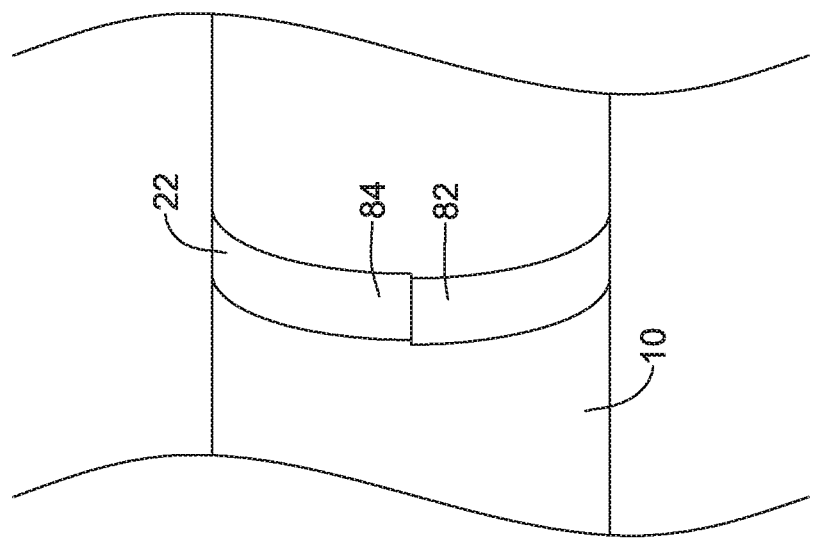

In some cases, it may be desirable to make two cuts in the anti-migration ring 22, thereby removing a section of the anti-migration ring 22 as illustrated in FIGS. 12A and 12B. In some cases, this may permit a larger reduction in stent diameter. In FIG. 12A, a first cut 76 and a second cut 78 have been made through the anti-migration ring 22, thereby freeing a section 80 of the ring that can be removed from the body lumen and creating a first cut end 82 and a second cut end 84. As can be seen in FIG. 12B, this permits a reduction in stent diameter as the first cut end 82 and the second cut end 84 meet up.

After cutting the anti-migration ring 22, 24, the support structure 26, may be at least partially collapsed to a smaller diameter and then the stent 10 may be withdrawn from the body lumen.

It will be appreciated that a variety of different materials may be used in forming the stent 10. In some embodiments, the covering 28 may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

The support structure 26 may be formed of any suitable desired material, such as a biocompatible material including biostable, bioabsorbable, biodegradable or bioerodible materials. For instance, the support structure 26 may be formed of a metallic material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the support structure 26 may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

The anti-migration rings 22, 24, 30, 70 may be formed of any suitable material, including the metals and polymers described with respect to the support structure 26 and the covering 28. In some embodiments, the anti-migration rings 22, 24, 30 may be stamped or laser cut from metals such as nitinol or stainless steel, for example. In some instances, the anti-migration rings 22, 24, 30 may be molded or otherwise formed of one or more polymeric materials such as nylon, ABS, PEEK, HDPE and polycarbonate. In some cases, the anti-migration rings 22, 24, 30 may be molded or otherwise formed of a biodegradable polymer such as PLA or PGA.

In some embodiments, the stent 10 may be coated with or otherwise include an elutable drug. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A tubular stent comprising:
   a stent body having a distal end and a proximal end;
   a covering surrounding at least a portion of the stent body;
   a first adjustable annular ring secured to the stent body within a lumen of the stent body, the first adjustable annular ring having a first end and a second end; and
   a second adjustable annular ring secured to the stent body within the lumen and spaced apart from the first adjustable annular ring;
   wherein the first adjustable annular ring is configured to permit movement of the second end relative to the first end to permit radial expansion of the first adjustable annular ring while resisting movement of the second end relative to the first end to prevent radial compression of the first adjustable annular ring;
   wherein the stent body is expandable from a compressed configuration having a first outer diameter to an expanded configuration having a second outer diameter larger than the first outer diameter;
   wherein radial expansion of the first and second adjustable annular rings enlarges regions of the stent body radially outward of each of the first and second adjustable annular rings at locations longitudinally aligned with each of the first and second adjustable annular rings to have a third outer diameter greater than the second outer diameter; and
   wherein the regions of the stent body having the third outer diameter are positioned longitudinally between portions of the stent body having the second outer diameter.

2. The tubular stent of claim 1, wherein the stent body is expandable, and the first and second adjustable annular rings are configured to expand in response to an expansive force applied to the stent body.

3. The tubular stent of claim 1, wherein the stent body comprises a braided structure including a plurality of wires braided together, and the first and second adjustable annular rings are mechanically secured relative to the braided structure.

4. The tubular stent of claim 1, wherein the first and second adjustable annular rings are adhesively secured to the stent body.

5. The tubular stent of claim 1, wherein the first adjustable annular ring comprises:
   a head at the first end of the first adjustable annular ring; and
   an elongate portion at the second end of the first adjustable annular ring that is passable through the head.

6. The tubular stent of claim 5, wherein the elongate portion interacts with the head such that the elongate portion is permitted to move in a first direction through the head but is prevented from moving in a second, opposite, direction through the head.

7. The tubular stent of claim 5, wherein the elongate portion has a rectilinear cross-sectional profile extending circumferentially around the first adjustable annular ring.

8. The tubular stent of claim 7, wherein the elongate portion comprises a plurality of angled teeth formed in at least one side of the elongate portion.

9. A stent configured to resist migration once implanted, the stent comprising:
a support structure extending from a distal end to a proximal end, the support structure defining an inner surface;
a first adjustable anti-migration ring secured to the inner surface of the support structure within a lumen of the stent; and
a second adjustable anti-migration ring secured to the inner surface of the support structure within the lumen of the stent and spaced apart from the first adjustable anti-migration ring;
wherein each of the first and second adjustable anti-migration rings includes a first end and a second end, and each of the first and second adjustable anti-migration rings is configured to permit movement of the second end relative to the first end to permit radial expansion of the first and second adjustable anti-migration rings while resisting movement of the second end relative to the first end to prevent radial compression of the first and second adjustable anti-migration rings;
wherein the support structure is expandable from a compressed configuration having a first outer diameter to an expanded configuration having a second outer diameter;
wherein radial expansion of the first and second adjustable anti-migration rings enlarges regions of the support structure radially outward of the first and second adjustable anti-migration rings at locations longitudinally aligned with the first and second adjustable anti-migration rings to have a third outer diameter greater than the second outer diameter; and
wherein a first end region of the support structure extending between the first adjustable anti-migration ring and the distal end has the second outer diameter and a second end region of the support structure extending between the second adjustable anti-migration ring and the proximal end has the second outer diameter.

10. The stent of claim 9, wherein the support structure comprises a braided metal structure.

11. The stent of claim 9, wherein the support structure comprises a laser cut tubular support structure.

12. The stent of claim 9, further comprising a covering surrounding at least a portion of the support structure.

13. The stent of claim 9, wherein at least one of the first adjustable anti-migration ring and the second adjustable anti-migration ring comprise:
a head including a ratchet mechanism; and
an elongate portion having a first end secured to the head and a second end that is passable through the head, the elongate portion including an integrated gear rack that is configured to interact with the ratchet mechanism such that the elongate portion is permitted to move in a first direction through the head but is prevented from moving in a second, opposite, direction through the head.

14. The stent of claim 13, wherein the elongate portion has a rectilinear cross-sectional profile extending circumferentially around the at least one of the first and second adjustable anti-migration rings.

15. The stent of claim 14, wherein the integrated gear rack comprises a plurality of angled teeth formed in at least one side of the elongate portion.

16. A stent configured to resist migration once implanted, the stent comprising:
a tubular support structure having a lumen extending from a distal end to a proximal end thereof;
a first adjustable anti-migration ring positioned within the lumen and secured to the tubular support structure; and
a second adjustable anti-migration ring positioned within the lumen and secured to the tubular support structure, the second adjustable anti-migration ring being spaced apart from the first adjustable anti-migration ring;
wherein each of the first and second adjustable anti-migration rings include a portion, a first end region, and a second end region and the portions are configured to permit movement of the second end region relative to the first end region to permit radial expansion of the first and second adjustable anti-migration rings while resisting movement of the second end region relative to the first end region to prevent radial compression of the first and second adjustable anti-migration rings;
wherein the tubular support structure is expandable from a compressed configuration having a first outer diameter to an expanded configuration having a second outer diameter larger than the first outer diameter;
wherein radial expansion of the first and second adjustable anti-migration rings enlarges regions of the tubular support structure radially outward of the first and second adjustable anti-migration rings at locations longitudinally aligned with the first and second adjustable anti-migration rings to have a third outer diameter greater than the second outer diameter; and
wherein the regions of the tubular support structure having the third outer diameter are positioned longitudinally between portions of the tubular support structure having the second outer diameter.

17. The stent of claim 16, wherein each of the first and second adjustable anti-migration rings includes a radially outwardly facing surface, an opposite radially inward facing surface, a first side surface extending from the radially outwardly facing surface to the radially inwardly facing surface, and an opposite second side surface extending from the radially outwardly facing surface to the radially inwardly facing surface;
wherein the first end region of the first adjustable anti-migration ring circumferentially overlaps the second end region of the first adjustable anti-migration ring;
wherein the first end region of the second adjustable anti-migration ring circumferentially overlaps the second end region of the second adjustable anti-migration ring;
wherein the first side surface of each of the first and second adjustable anti-migration rings includes an integrated gear rack comprising a plurality of angled teeth.

18. The stent of claim 17, wherein the first side surface of the first anti-migration ring faces the second side surface of the first adjustable anti-migration ring; and
the first side surface of the second anti-migration ring faces the second side surface of the second adjustable anti-migration ring.

* * * * *